United States Patent
Porter et al.

(10) Patent No.: US 6,413,775 B1
(45) Date of Patent: Jul. 2, 2002

(54) POLYAMINE ANALOG-ACTIVATED SSAT GENE THERAPY

(75) Inventors: Carl W. Porter, East Aurora; Slavoljub Vujcic, Amherst; Debora Kramer, East Aurora; Kristen Kee, Kenmore, all of NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 09/608,330

(22) Filed: Jun. 29, 2000

Related U.S. Application Data

(60) Provisional application No. 60/152,857, filed on Sep. 8, 1999, and provisional application No. 60/144,542, filed on Jul. 16, 1999.

(51) Int. Cl.[7] ............... C12N 15/87; C12Q 1/68; C12P 19/34; C07K 17/00; C07H 21/04
(52) U.S. Cl. ............. 435/455; 435/6; 435/91.1; 530/350; 536/23.1
(58) Field of Search .............. 435/6, 455, 456, 435/458, 15, 91.1, 91.21; 530/350, 358; 536/23.1

(56) References Cited

PUBLICATIONS

Parry et al. Post–transcriptional regulation of the content of spermidine/spermine N1–acetyltransferase by N1N12–bis(ethyl)spermine 1995.*

Parry et al, Post–transcriptional regulation of the content of spermidine/spermine N1–acetyltransferase by N1N12–bis(ethyl)spermine, Biochem J. (1995), 451–452 (1995).*

Robbins, Paul D. et al, Viral Vectors for Gene Therapy, Pharmacol. Ther., vol. 80, No. 1, 1998, p. 41.*

Friedman, Theodore, Overcoming the Obstacles, Scientific American, Jun. 1997, pp. 99–100.*

Schofiel, J. P. et al, Non–viral Approaches to Gene Therapy, British Medical Bulletin, vol. 51 No. 1, 1995, p. 63.*

Amundson et al, Fluorescent cDNA microarray hybridization reveals complexity and heterogeneity of cellular genotoxic stress responses, Onocogene, vol. 18, 1999.*

CAS Registry, No. 121749–39–1, N1, N11 diethylnorspermine.*

CAS Registry, No. 61345–84–4, N1, N12 bis(ethyl)spermine.*

Bergeron, et al, 1997, J. Med. Chem. 40:1475–1494.

Porter, et al, 1992, Falk Symposium on Polyamines in the Gastrointestinal Tract, Edited by R.H. Dowling, U.R. Fosch, and Chr. Loser, Kluwer Academic Publishers, Dordrecht, 1992, pp. 301–322.

Casero, et al, 1989, Cancer Res., 49:3829–3833.

Porter, et al, 1991, Cancer Res. 51:3715–3720, 1991.

Shappell, et al, 1992, Anticancer Res. 12:1083–1090.

Pietilä, et al, 1997, J. Biol. Chem . 272:18746–18751.

Alhonen, et al, 1998, J. Biol. Chem. 273:1964–1969.

McCloskey, et al, 1999, J. Biol. Chem. 274, 6175–6182.

* cited by examiner

Primary Examiner—Remy Yucel
Assistant Examiner—Konstantina Katcheves
(74) Attorney, Agent, or Firm—Hodgson Russ LLP

(57) ABSTRACT

The present invention provides a novel method to increase both the antitumor potency and the selectivity of DENSPM, a polyamine analog. The method comprises the steps increasing the amount of SSAT mRNA, and delivering a therapeutically sufficient dose of DENSPM which allows conversion of SSAT mRNA to enzyme activity, polyamine pool depletion and growth inhibition. The SSAT mRNA may be increased by conditionally induced overexpression of SSAT, or by modulating the transcriptional regulation of the endogenous SSAT gene.

3 Claims, 10 Drawing Sheets

*Figure 1*
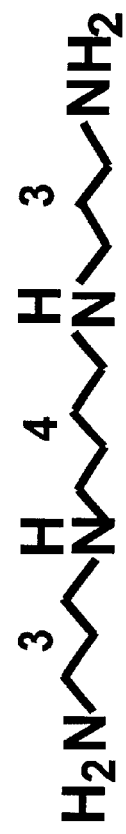
Spermine
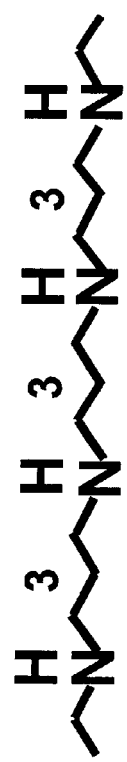
DENSPM
*($N^1$, $N^{11}$-diethylnorspermine)*

Figure 3
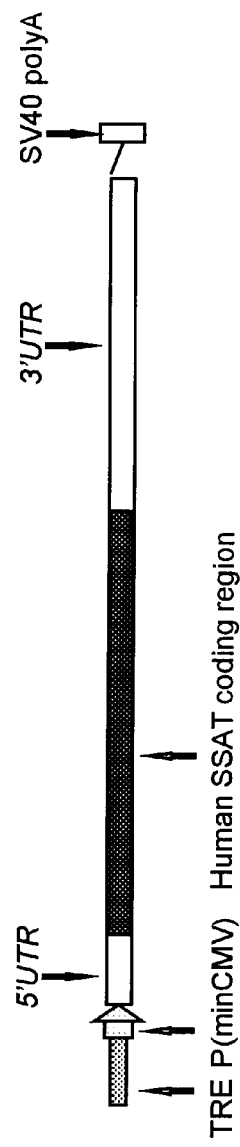
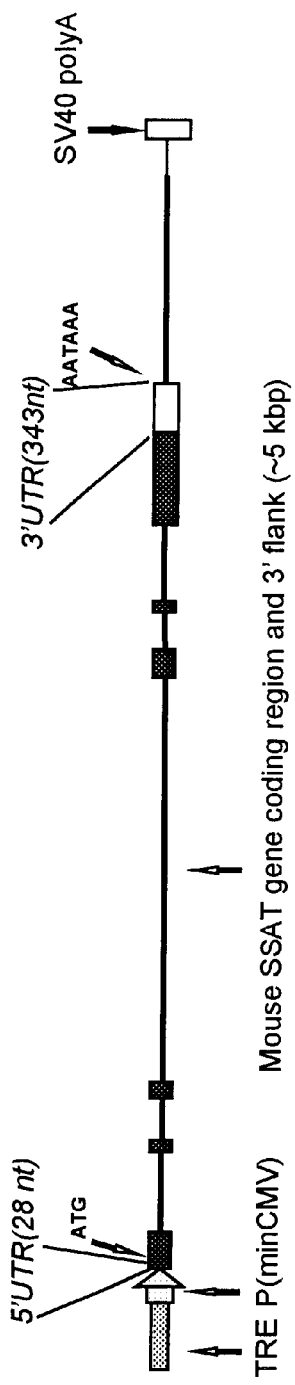

POLYAMINE ANALOG-ACTIVATED SSAT GENE THERAPY

This application claims the priority of U.S. provisional patent application Ser. No. 60/152,857 filed on Sep. 8, 1999; and U.S. provisional patent application Ser. No. 60/144,542 filed on Jul. 16, 1999.

This work was supported by NIH Award R01-CA-76428 and U.S. Army Contract no. DAMD17-98-1-8487. The government has certain rights in the invention.

FIELD OF THE INVENTION

This invention relates generally to the field of anti-tumor therapies. More particularly, this invention provides a method for enhancing the anti-tumor potency and selectivity of certain polyamine analogs. Viewed alternatively, it may be regarded as a drug activated suicide gene therapy.

DESCRIPTION OF RELATED ART

The polyamine analog $N^1$, $N^{11}$ diethylnorspermine (DENSPM, FIG. 1) is currently undergoing clinical evaluation against various solid tumors (Bergeron et al., 1997, J. Med. Chem. 40: 1475–1494; Porter et al., 1992, *Falk Symposium on Polyamines in the Gastrointestinal Tract*, Edited by R. H. Dowling, U. R. Folsch, and Chr Loser, Kluwer Academic Publishers, Dordrecht, 1992, pp. 301–322). Under in vitro growth inhibitory conditions, the analog depletes polyamine pools by down-regulating the key polyamine biosynthetic enzymes, ornithine and S-adenosylmethionine decarboxylase, and potently up-regulating the polyamine catabolic enzyme, spermidine-spermine $N^1$-acetyltransferase (SSAT). In many tumor cells, induction of SSAT activity may exceed 1000-fold and this may represent the most potent gene response to any small molecule anticancer agent. Because polyamines, and particularly spermidine, are required for cell growth (Mamont et al., 1978, Biochem. Biophys. Res. Commun. 81:58–66; Kramer et al., 1989, Biochem J. 259:325–331) antiproliferative strategies designed to selectively deplete these molecules from cancer cells have emerged as experimental anticancer therapies (Marton and Pegg, Ann. Rev. Pharmacol. 195, 35:55–91). Induction of SSAT now appears to be a novel means to achieve polyamine pool depletion.

Potent induction of SSAT by DENSPM has been known for some time (Porter et al., supra; Casero et al., 1989, *Cancer Res.*, 49:3829–3833) and several groups have attempted to determine the role of this response in analog mediated growth inhibition. Several lines of evidence support the relationship between SSAT induction and inhibition of cell growth. It is known that both polyamine pool depletion and cell growth inhibition of various cell lines by DENSPM correlates with the extent to which SSAT is induced (Casero et al., 1989, supra; Porter et al., 1991, *Cancer Res.* 51:3715–3720, 1991; Shappell et al., 1992, *Anticancer Res.* 12:1083–1090). Analogs that differentially induce SSAT within a single cell line, inhibit cell growth in a manner that is highly correlative with enzyme induction Porter et al., 1991, supra; Kramer et al., 1999, *Cancer Res.* 59:1278–1286). In other studies, murine embryonic fibroblasts derived from transgenic mice that systemically over-express SSAT were observed to be more growth sensitive to DENSPM than those from parental animals (Pietilä et al., 1997, J. Biol. Chem. 272:18746–18751; Alhonen et al., 1998, J. Biol. Chem. 273:1964–1969). Finally, DENSPM resistant CHO cells have been shown to be unable to induce high levels of SSAT activity (McCloskey et al., 1999, *Proc. Am. Assoc. Cancer Res.* 40:302).

While the above observations suggest that induction of SSAT is correlated with inhibition of cell growth, stable over-expression of SSAT does not appear to affect growth rate. It was observed that fibroblasts from transgenic mice that overexpress SSAT, grew at approximately the same rate as parental fibroblasts. A similar observation was recently made with CHO cells transfected with SSAT (McCloskey et al., 1999, J. Biol. Chem. 274, 6174–6182).

Thus, the role of SSAT in growth inhibition at the time of the studies described below was uncertain and despite the known inhibitory effects of DENSPM, in the absence of a clear understanding of the role of SSAT, its anti-tumor effects have not been fully elucidated. Such information could provide valuable strategies for the use and development of polyamine analogs as novel anti-tumor therapies. More particularly, induction of SSAT would provide a useful alternative to the use of polyamine inhibitors and analogs as a novel means to deplete intracellular polyamine pools and inhibit cell growth.

SUMMARY OF THE INVENTION

The present invention discloses a method for increasing the anti-tumor potency and selectivity of DENSPM, a polyamine analog. The present method is based on the unexpected observation that increasing the amount of SSAT mRNA, depletes certain polyamine pools, inhibits cell growth and significantly increases the effectiveness of DENSPM. In one embodiment of the invention, SSAT activity is increased by conditional overexpression of SSAT mRNA. In another embodiment, SSAT activity is increased by using a polyamine analog to markedly enhance the expression of the endogenous SSAT gene.

An object of the present invention is to increase the antitumor effectiveness of DENSPM by overexpressing SSAT MRNA prior to treatment with the analog.

Another object of the present invention is to increase the effectiveness of DENSPM by the use of drugs, radiation or factors that enhance transcription of the endogenous SSAT gene.

Another object of the present invention is to provide a conditionally activated gene therapy wherein the induction of SSAT is placed under the control of tissue-specific gene promoter, followed by treatment with DENSPM.

BRIEF DESCRIPTION OF THE DRAWINGS

FIG. 1 is a representation of the natural polyamine spermine and the polyamine analog DENSPM.

FIG. 3 is a representation of the constructs used for transfection of Dox-regulatable human SSAT cDNA and murine SSAT genomic sequences into MCF-7 cells.

DETAILED DESCRIPTION OF THE INVENTION

The term "inhibition of cell growth" for the purposes of specification and claims means an inhibition of the increase in the number of cells or the exhibition of cytotoxic effects leading to a decrease in cell number.

The present invention comprises a novel method to increase both the antitumor potency and the selectivity of a polyamine analog, DENSPM. Potency is enhanced by rapid and massive production of SSAT activity. At the same time, selectivity is enhanced, primarily, by the tissue specific promoter/enhancer system, which regulates gene expression at the level of transcription. Selectivity may be further enhanced by direct intratumoral delivery i.e., brachytherapy and any tropism conferred by an appropriately selected viral gene transfer system including replicating viral systems which selectively propagate in tumor cells which have defective cell cycle regulatory proteins (Bischoff et al., 1996, Science 274:373–376.

Figure 2:
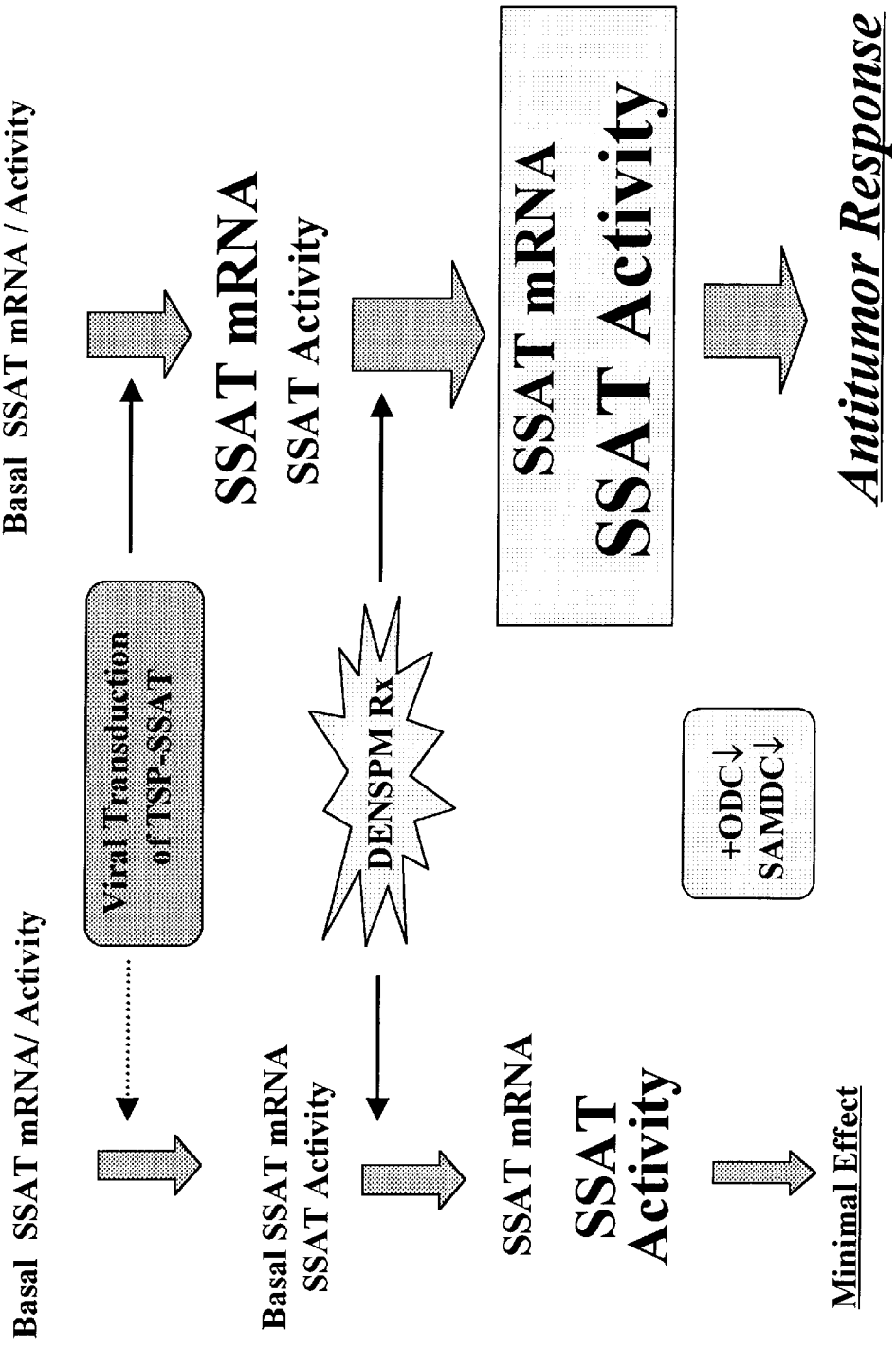
FIG. 2 is a schematic representation of DENSPM-activated SSAT gene therapy strategy (TSP, Tissue Specific Promoter/Enhancer).

The invention is best illustrated by the following example outlined as a series of steps in FIG. 2. (a) SSAT cDNA is placed under the control of a tissue-specific core promoter/ enhancer system and packaged into a viral delivery system; (b) the viral system is initially introduced directly into a tumor or it could be systemically delivered; (c) a systemically delivered dose(s) of DENSPM is administered; (d) virally transduced SSAT mRNA is post-transcriptionally converted by DENSPM to massive amounts of DENSPM activity. Because more MRNA is contained within the targeted tissues, the greater SSAT activity and antiproliferative and antitumor activity is registered there.

As an alternative to introducing an exogenous SSAT expression system, genes or factors capable of enhancing the transcriptional regulation of the endogenous SSAT gene could also be utilized. More particularly, factors and co-factors specifically involved in the transcriptional activation of SSAT gene expression by analogs could be utilized to increase expression of the endogenous gene. As an example, Wang et al. (J. Biol. Chem. 274:22095–22101, 1999, the disclosure of which is incorporated herein by reference) recently identified a co-factor involved in the transcriptional activation of SSAT by polyamines and polyamine analogs such as DENSPM. They further demonstrate that this gene appears to be selectively increased in cells which are responsive to SSAT induction by polyamine analogs such as DENSPM—these same cells were previously shown to be more sensitive to the growth inhibitory effects of polyamine analogs (Casero et al., 1989, Cancer Res. 49:3829–3833). Thus, by introducing either exogenous SSAT or factors that stimulate transcription of the endogenous SSAT gene, the end net result will be an accumulation of SSAT MRNA. In the presence of analogs, this will be translationally and post-translationally amplified, leading to selective production of SSAT activity and growth inhibition in those cell types targeted by the gene therapy promoter strategy.

As another alternative to introducing an exogenous SSAT expression system, drugs or therapeutic manipulations such as irradiation that are capable of enhancing the transcriptional regulation of the endogenous SSAT gene could also be utilized. As an example, Amundson et al. (1999, Oncogene 18, 3666–3672, the disclosure of which is incorporated herein by reference) recently reported that exposure of cells to ionizing radiation causes a significant induction of SSAT mRNA as determined by microarray hybridization. Thus, DENSPM or related polyamine analogs could be used to enhance the conversion of this MRNA to activity and to augment the antiproliferative response.

SSAT mRNA and activity are induced by many spermidine and spermine analogs (Libby et al., 1989, *Biochem. Pharmacol.*, 38:1435–1442; Porter et al., 1991, *Cancer Res.*, 51:3715–3720; Fogel-Petrovic et al., 1997, 52:69–74; Kramer et al., 1997, *Cancer Res.* 57:5521–5527; Casero et al., 1995, *Cancer Chemo. Pharmacol.* 36:69–74; Bergeron et al., 1995, *Med. Chem.* 38:2278–2285, Table 4). These analogs are referred to in the present application as polyamine analogs. Typically, these include spermine and spermine analogs in which the terminal amines are alkylated with aliphatic and aromatic substituents or in which the interamine carbons are varied or replaced with aromatic groups. Structure-function analysis (Fogel-Petrovic et al., 1997, supra) indicates that induction of SSAT mRNA is most influenced by intra-amine carbon distances with aminopropyl moieties being the most effective. By contrast, enzyme activity was most potently determined by terminal N-alkyl substitutents with ethyl groups being the most effective. Because DENSPM contains three aminopropyl units and two N-ethyl groups, it potently induces SSAT mRNA and effectively stabilizes SSAT enzyme protein. Thus, DENSPM produces the greatest increase in enzyme activity of any spermidine or spermine analog characterized to date (Fogel-Petrovic et al., ibid). However, it should be noted that polyamine analogs exert differential effects on cell cycle progression and apoptosis (Kramer et al., 1997, supra) in cells and have different toxicological and antitumor effects in animals (Bernacki et al., 1992, Cancer Res. 52:2424–2430). These effects may be independent of SSAT induction. Thus, although DENSPM is currenly being used clinically, all other spermidine or spermine analogs capable of post-transcriptionally amplifying SSAT expression are included in the present invention strategy since they may prove to be more pharmacologically useful than DENSPM in the context of patients.

The invention can also be viewed as a conditionally regulated suicide gene therapy. Thus, using SSAT (or a related regulatory gene) as a suicide gene therapy candidate (s) for gene therapy, placing it under the transcriptional control of a tissue-specific gene promoter, and post-transcriptionally activating it with DENSPM are the essential features of this invention. DENSPM is capable of enhancing SSAT gene expression at the level of mRNA stabilization (Fogel Petrovic et al., 1997, J. Biol. Chem. 268:19118–19125) translation (Fogel-Petrovic et al. 1996 FEBS Lett 391:89–94.) and protein stabilization (Libby et al., 1989, Biochem. Pharmacol. 38:1435–1442; Casero et al., 1990, Biochem. J. 270:615–620; Coleman et al., 1995, Biochem. 34:13423–13430). It will be recognized by those skilled in the art that while data is presented herein for activating conditionally regulated SSAT, the method of the present invention can be applied to any suicide gene/activator system.

The gene therapy method described below is predicated on the novel finding that conditional induction of SSAT is directly related to growth inhibition, and that DENSPM efficiently amplifies modestly elevated MRNA levels to large amounts of enzyme activity leading to polyamine depletion and growth inhibtion. The ability to achieve tumor or organ selectivity with tissue-specific gene promoters can be advantageously used to target the desired site. Different tumors can be targeted by using tissue specific promoters. For example, tissue-specific promoters such as tyrosinase would be appropriate for targeting melanoma while prostate-specific antigen (PSA), probasin, prostate-specific membrane antigen (PSMA) or various other prostate-specific proteins would be well-suited for targeting prostate carcinoma. For tumors of the nervous system, promoters that can be used include, but are not limited to, the glial fibrillary acidic protein (GFAP) promoter, the neuron specific enolase (NSE) promoter, neurotransmitter promoters (e.g., tyrosine hydroxylase, choline acetyltransferase), and promoters for neurotrophic factors (e.g., nerve growth factor, NT-3, brain derived growth factor and the like). It is preferable to use both the core promoter and enhancer regions in order to obtain maximal gene expression.

The method of the present invention could be applied to any tumor for which there are tissue or tumor specific gene promoters. The invention is intended to cover all of these possibilities. For example, the SSAT gene therapy system could be used to target prostate carcinoma. In addition to the clinical importance of this pathological condition, several well characterized gene promoter/enhancer systems with high selectivity towards prostate tissue and prostate carcinoma are available (Brookes et al., 1998, *The Prostate* 35:18–26). Further, organ and primary tumors are accessible for brachytherapy via transperineal delivery (which is now widely applied and well known to those skilled in the art, Blasko et al., 1994, *Semin. Rad. Oncol.* 3:240–249). The accessibility of the organ and primary tumors for biopsy and clinical evaluation and, the possible collateral therapeutic indication in benign prostate hyperplasia (BPH) also make this condition amenable to the method of the present invention. In addition the above rationale, the prospects for selectivity towards prostate carcinoma by polyamine-directed strategies, is enhanced by the fact that the gland represents the richest source of polyamine biosynthesis in the body and is the only tissue to synthesize polyamines for export (into semen). As such, the prostate and tumors derived from it may, have altered regulatory mechanisms that control polyamine homeostasis (including uptake)(Mi et al., 1998, The Prostate, 35:51–60), and these could further contribute to the selectivity of the gene/drug system.

Another example of a tumor that can be targeted using the method of the present invention is melanoma, in which case the tissue/tumor specific promoter/enhancer can be tyrosinase, a key enzyme in the synthesis of melanin pigment. An advantage of using the method of the present invention for this disease is the ease of direct intratumoral injection of the gene therapy system. If multiple foci are available in the same patient, responses to DENSPM can be compared in directly injected and non-injected tumors. There exists the additional advantage that melanoma typically induces large amounts of SSAT (Porter et al., 1992, supra) and has shown some responses in ongoing clinical trials.

To introduce SSAT cDNA into a tumor, a viral vector can be used. The SSAT cDNA (or that of a related regulatory gene) is inserted into the viral genome. Regulatory elements to direct the expression of the gene product can be included with the SSAT cDNA. The regulatory elements may include tissue-specific promoters as described above. Different viral vectors which can be used for the purposes of introducing the SSAT cDNA into tumor cells include, but are not limited to, adenoviruses, adeno-associated viruses, herpes viruses, and replication-defective retroviruses. It also includes viral systems which are only capable of replicating in tumor cells which are defective in critical proteins required for regulation of cell cycle such as p53 and others (Bischoff et al., 1996, supra) In addition to viral vectors, other transfer methods based on mechanisms used by mammalian cells for cellular uptake of macromolecules such as liposomal derived systems, poly-lysine conjugates and the like can also be used.

The role of post-transcriptional regulation by DENSPM is important since it allows for the tissue specific expression of SSAT mRNA prior to post-transcriptional activation and amplification with the analog. Most systems designed to conditionally regulate gene expression involve transcriptional control (i.e. the tetracycline system) which could preclude the use of tissue specific promoters to achieve tumor selectivity. However, the present invention allows for tissue-specific MRNA expression via promoter systems followed by the potent amplification of this response with DENSPM. Of particular advantage is the fact that the intensity of the gene response can be clinically controlled by DENSPM dosing. Moreover, since the gene is expected to persist in infected tumor cells that survive the first DENSPM treatment, a second round of treatment could be used without needing to introduce another round of viral transfection.

In another embodiment, a conditionally regulated system can be used to alter the expression of SSAT. An example of a system that can be used is the tetracycline dependent gene expression system (Clonetech). This provides regulated and reversible control of gene expression. To induce the expression of SSAT upon a stimulus, the Tet-On™ system can be used. The Tet-Off™ system provides induction of expression upon removal of a stimulus. This system uses a chimeric transactivator to activate transcription of the SSAT gene. The transactivator can be expressed from the constitutive CMV promoter or it can be expressed from a tissue-specific promoter. In the Tet-On system, the transactivator binds to the Tet responsive element in the presence of an activator (tetracycline or its analogs such as doxycycline), and activates transcription in the presence of the activator. Further, in one variation of this embodiment, a retroviral system (RevTet-On™) can be used to deliver the Tet vectors to cells.

Following the delivery of tetracycline expression vectors to cells, the expression of SSAT can be induced by administration of an activator, such as doxycycline. SSAT gene expression can be further amplified by subsequent administration of DENSPM.

The method of the present invention will be better understood by the following embodiments which are to be construed as illustrative and not restrictive.

EXAMPLE 1

This embodiment illustrates the construction of a conditionally regulated expression vector containing SSAT cDNA.

Cloning

An EcoRI fragment containing the complete human SSAT cDNA (Xiao et al., 1991, *Biochem. Biophys. Res. Commun.* 179, 407–415 was cloned into an expression vector purchased from Clontech Laboratories which contained a Tetracycline responsive element (TRE). Similarly, an FspI—BamHI fragment containing a major portion of the murine SSAT gene (Fogel-Petrovic et al., 1993, *Biochim. Biophys Acta* 1216, 255–264) lacking the 5' flanking region and all except the first 28 nucleotides of the 5' UTR of first exon was also cloned into a pTRE expression vector (FIG. 3).

Cell Cultures

A MCF-7 breast carcinoma cell line stably transfected with a tetracycline-off transfection system was purchased from Clontech Laboratories Inc. (Palo Alto, Calif.). The cells were cultured in Dulbecco's Modified Eagle's Medium (DMEM; Life Technologies, Gaithersburg, Md.), supplemented with 2 mM glutamine, 10% fetal bovine serum, penicillin at 100 U/ml, streptomycin at 100 U/ml and the antibiotic G418 (Life Technologies) at 100 µg/ml at 37° C. in the presence of 5% $CO_2$. Cells were harvested by trypsinization and counted electronically (Coulter Model ZM, Coulter Electronics, Hialeah, Fla.). During treatment with polyamines or analogs, 1 mM aminoguanidine was routinely included in the media to prevent enzymatic oxidation to toxic products.

Analytical Methods

Total RNA was extracted with guanidine isothiocyanate and purified by the commonly used cesium chloride gradient centrifugation. Human SSAT cDNA probe (Xiao et al, 1991, supra) was used in Northern blot analyses. ODC and SSAT enzyme activities were assayed as reported earlier (Kramer et al., 1995, *J. Biol. Chem.* 270, 2124–2132.31). Polyamines, their acetylated derivatives and the polyamine analog DENSPM were measured by high performance liquid chromatography as previously described in detail by Kramer et al. (Kramer et al., 1993, supra), which method is incorporated herein by reference.

EXAMPLE 2

This embodiment illustrates the transfection of cells in vitro with conditionally regulated SSAT cDNA.

Transfection and Conditional Expression

To enhance the growth inhibitory effects of DENSPM, and to more definitively examine the relationship between SSAT overexpression and cell growth, a cell line was developed in which SSAT expression is conditionally regulated by doxycycline (DOX) an analog of tetracycline which penetrates cells more effectively. MCF-7 cells containing the pTet-Off plasmid were transfected with the PTRE/ expression plasmids described above using the Lipofectin method (Notarangelo et al., 1997, Focus, 19, 58–59, incorporated herein by reference). To facilitate clone selection, cells were co-transfected with a pTK-Hyg vector (Clontech Laboratories, Inc.). Transfected clones resistant to 100 mg/ml hygromycin were selected and tested for SSAT enzyme activity and/or mRNA in the presence or absence of 200 ng/ml Dox [+Dox and -Dox, respectively (Clontech Laboratories, Inc)]. In the presence of Dox, SSAT transcription is closed; in the absence of Dox, SSAT transcription is open. The concentration of 200 ng/ml was found to be the minimum antibiotic concentration required to fully and consistently suppress SSAT gene expression during cell culture passage. Clones, which expressed the lowest basal levels of SSAT activity or mRNA in +Dox and the greatest induced level of SSAT activity or mRNA -Dox, were selected for further study. Clones were maintained continuously under +Dox conditions until experiments were initiated.

Derivation and Selection of Transfectants

Figure 4:
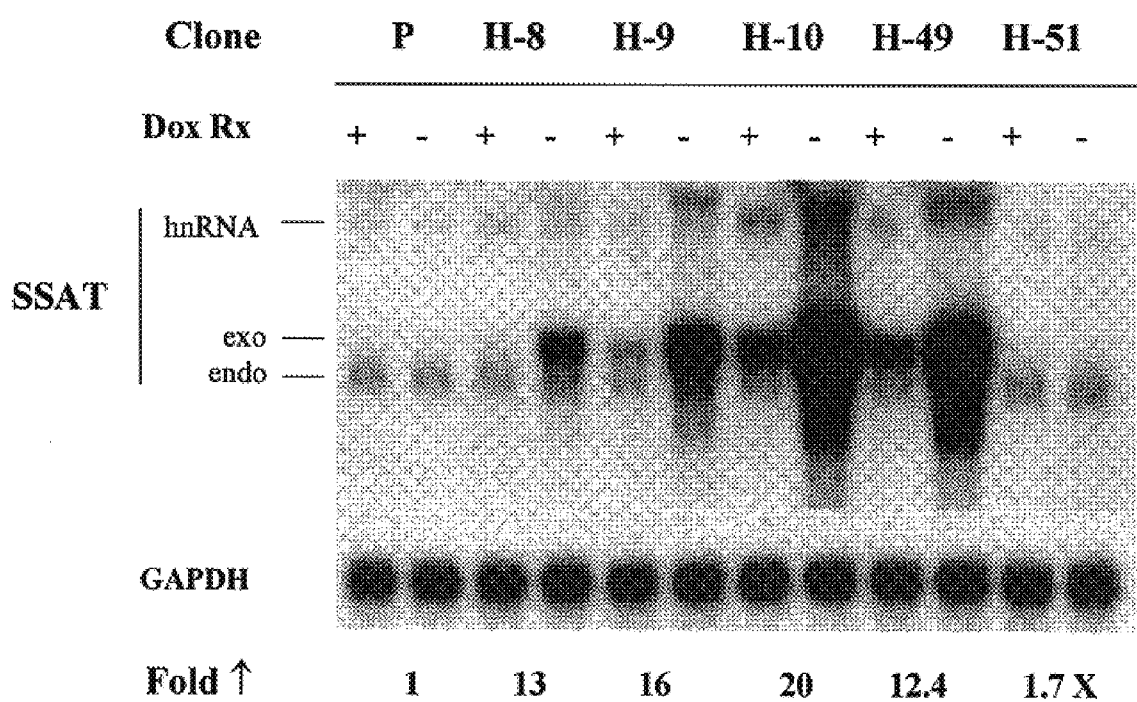
FIG. 4 is a photographic representation of Northern blot analysis of SSAT mRNA in example clones of MCF-7/hSc cells transfected with the human SSAT cDNA under a Dox-Off conditional promoter system (P, parental nontransfected cells). H-10 was selected for further study because it had the greatest SSAT MRNA differential under –Dox (open) and +Dox (closed) conditions.

Cells transfected with either the human SSAT cDNA (MCF-7/hSc) or the murine SSAT gene (MCF-7/mSg) were selected in hygromycin and grown as clones in the presence of Dox (Example clones are shown in FIG. 4). Of eleven MCF-7/hSc clones, those most sensitive to Dox regulation were selected according to the differential between SSAT mRNA in the presence of Dox (closed system) versus mRNA in the absence of Dox (open system). Attention focused on clone H-10 which displayed a 20-fold increase in SSAT mRNA (FIG. 4) following Dox removal for 48 h. The SSAT mRNA from the transfected human cDNA (~1.5 kb) was clearly distinguishable from the smaller (~1.3 kb) endogenous transcript presumably because of differences in polyadenylation, which we have previously shown to be affected by enzyme induction (Fogel-Petrovic et al., 1993 supra). An unexpected finding was the appearance two bands in the region of ~3.5 kb SSAT RNA that correlate with heteronuclear (hnRNA) in origin. These are not likely to have originated from the cDNA, and therefore it is possible that enzyme induction may interfere with processing of the endogenous transcripts.

The same selection strategy was also applied to MCF-7 cells transfected with the murine SSAT gene (MCF-7/mSg cells) and lead to the identification of the M-3 clone. The M-3 clone showed a ~3-fold increase in SSAT mRNA following Dox removal for 48 h. As expected for transfected genomic sequences, this SSAT mRNA was apparent as mature ~1.3 kb species comparable in size to the endogenous message and as a less abundant preprocessed ~3.5 kb RNA.

EXAMPLE 3

This embodiment illustrates that SSAT is functionally expressed in transfected cells.

SSAT Expression in Selected Clones

Figure 5:
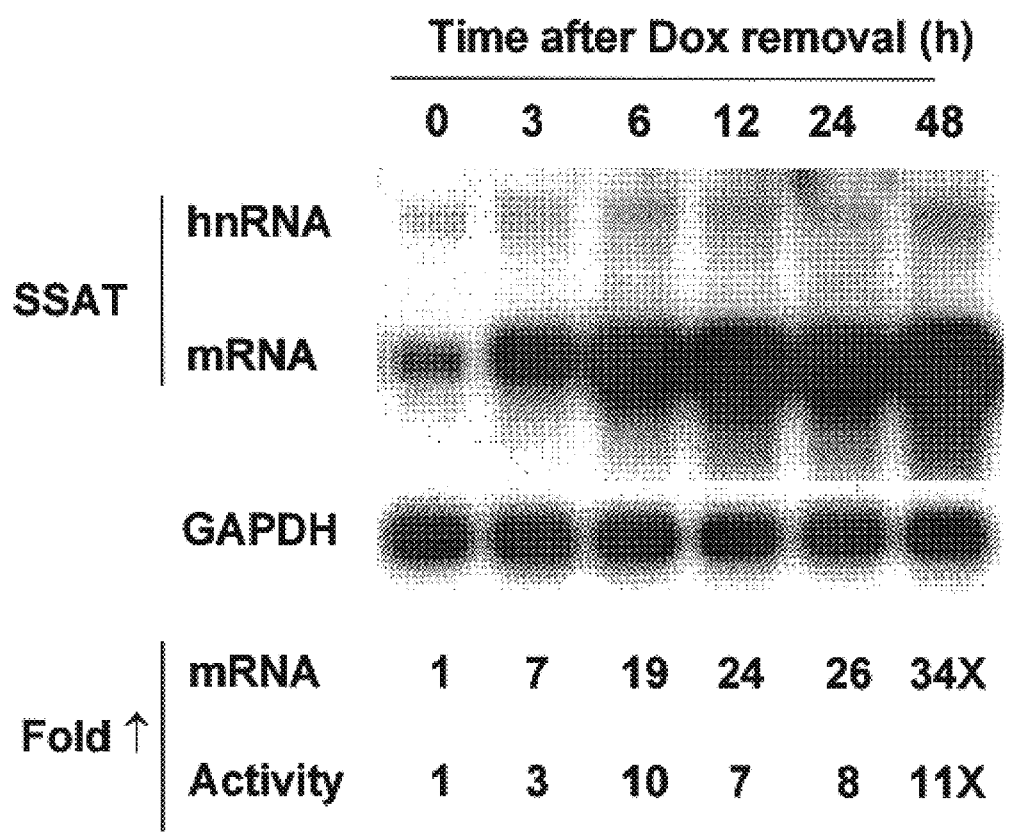
FIG. 5 is a photographic representation of a Northern blot analysis of SSAT MRNA in clone H-10 cells following removal of 200 ng/ml Dox (open system). Clone H10 cells are transfected with human SSAT cDNA under a Tet-off inducible promoter.

The time-dependence of Dox-regulated expression of SSAT MRNA and activity was characterized in the newly selected H-10 clone (FIG. 5). Following Dox-removal, message increased most rapidly during the first 6 h after-which it reached a plateau which typically ranged between 20- to 30-fold. This induction of MRNA was accompanied by a more modest rise in SSAT activity that varied within the 5- to 10-fold range (FIG. 5 and Table 1). In the case of M-3 cells, the modest 3-fold increase in mRNA was also accompanied by an increase in SSAT activity similar to that seen in the H-10 cells.

Effects of SSAT over-expression on Polyamine Metabolism

Figure 6:
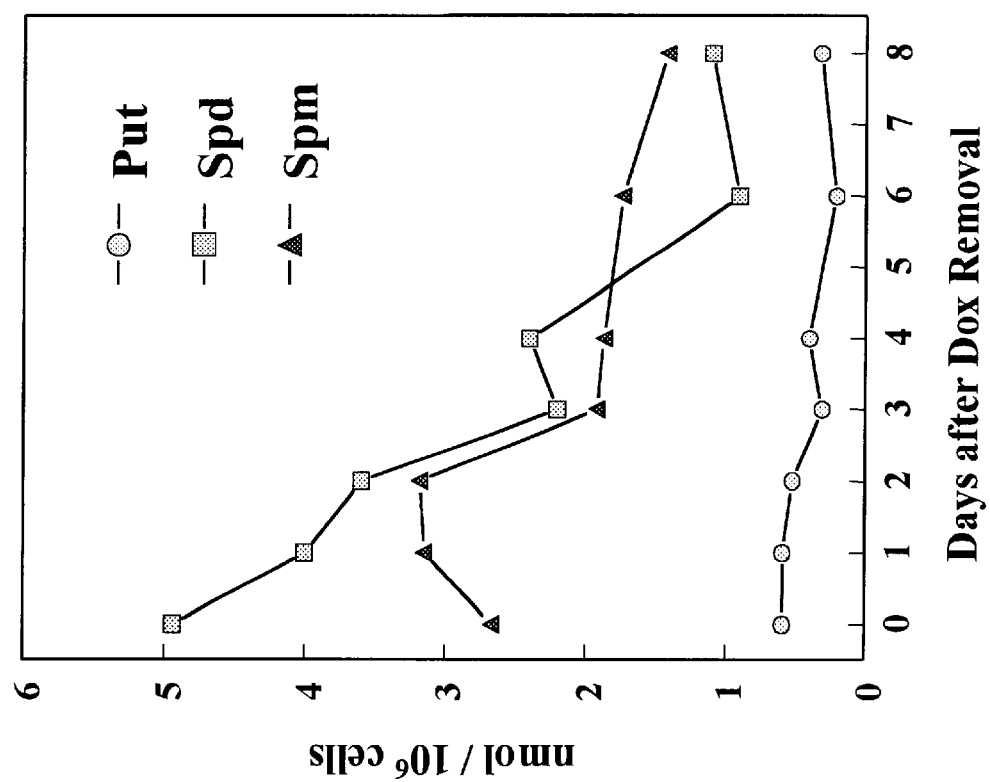
FIG. 6 is a graphic representation of the progressive depletion of polyamine pools following Dox removal (open system). Note that spermidine (Spd) is most affected.

The time-dependent metabolic consequences of SSAT overexpression on polyamine metabolism were evaluated in the H-10 clone (Table 1). In this table is presented a tabulation of the time-dependent effects of conditional overexpression (closed vs open) on ornithine decarboxylase activity (no effect) SSAT activity (induced) and natural and acetylated polyamine pools. Note that Spd pools are progressively depleted. Interestingly, there did not appear to be a compensatory rise in ODC activity as has been seen in systems bearing stably transfected SSAT (Pietilä et al., 1997, *J. Biol. Chem.*, 272, 18746–1875113; Alhonen et al., 1998, *J. Biol. Chem.* 273, 1964–1969; McCloskey et al., 1999, *J. Biol. Chem.* 274:61745–61752). The typical 5- to 10-fold increase in SSAT activity was seen to have an obvious effect on polyamine pools. Following 48 h -Dox, Put pools were lowered by >30% relative to zero time, Spd by ~70% while Spm was largely unaffected. At 96 h, Spd pools were further decreased to <15% of the zero control indicating the progressive effect of SSAT overexpression. A detailed analysis of the progressive nature of polyamine pool effects is shown in FIG. 6 where the more obvious effect on Spd pools is apparent. Consistent with SSAT enzymatic function, acetylated polyamine pools were profoundly increased. $N^1$-acetylSpd, increased from barely detectable levels to 680 and 1545 pmol/$10^6$ cells by 48 and 96 h, respectively. The other enzyme product $N^1$-acetylSpm which was rarely seen in most cells increased from <5 in +Dox cells to 140 pmol/$10^6$ cells in −Dox cells at 96 h. We also noted significant amounts of a novel polyamine peak that was subsequently identified as $N^1,N^{12}$-diacetylSpm.

Very similar trends were observed in M-3 cells transfected with murine SSAT genomic sequences (MCF-7/mSg cells, Table 1). As with the H-10 cells, the greatest effect involved depletion of Spd pools which fell to ~80% of control by 96 h. Overall, the polyamine pools changes seen in both of these cell clones were characteristic of activated polyamine catabolism as previously described in SSAT transgenic mice (Pietilä et al., 1997, *J. Biol. Chem.*, 272, 18746–1875113), in fibroblasts derived from them (Alhonen et al., 1998, *J. Biol. Chem.* 273, 1964–1969), and in various human tumor cells treated in vitro (Casero et al., 1989, *Cancer Res.* 49, 3829–383310; Pegg et al., 1989, *J. Biol. Chem.* 264 11744–11749; Porter et al., 1991, *Cancer Res.* 51, 3715–3720) or in vivo (Fogel-Petrovic et al., 1993, *J. Biol. Chem.* 268, 19118–1912533) with DENSPM. In these previously reported systems, cell growth was not affected.

EXAMPLE 4

Figure 7:
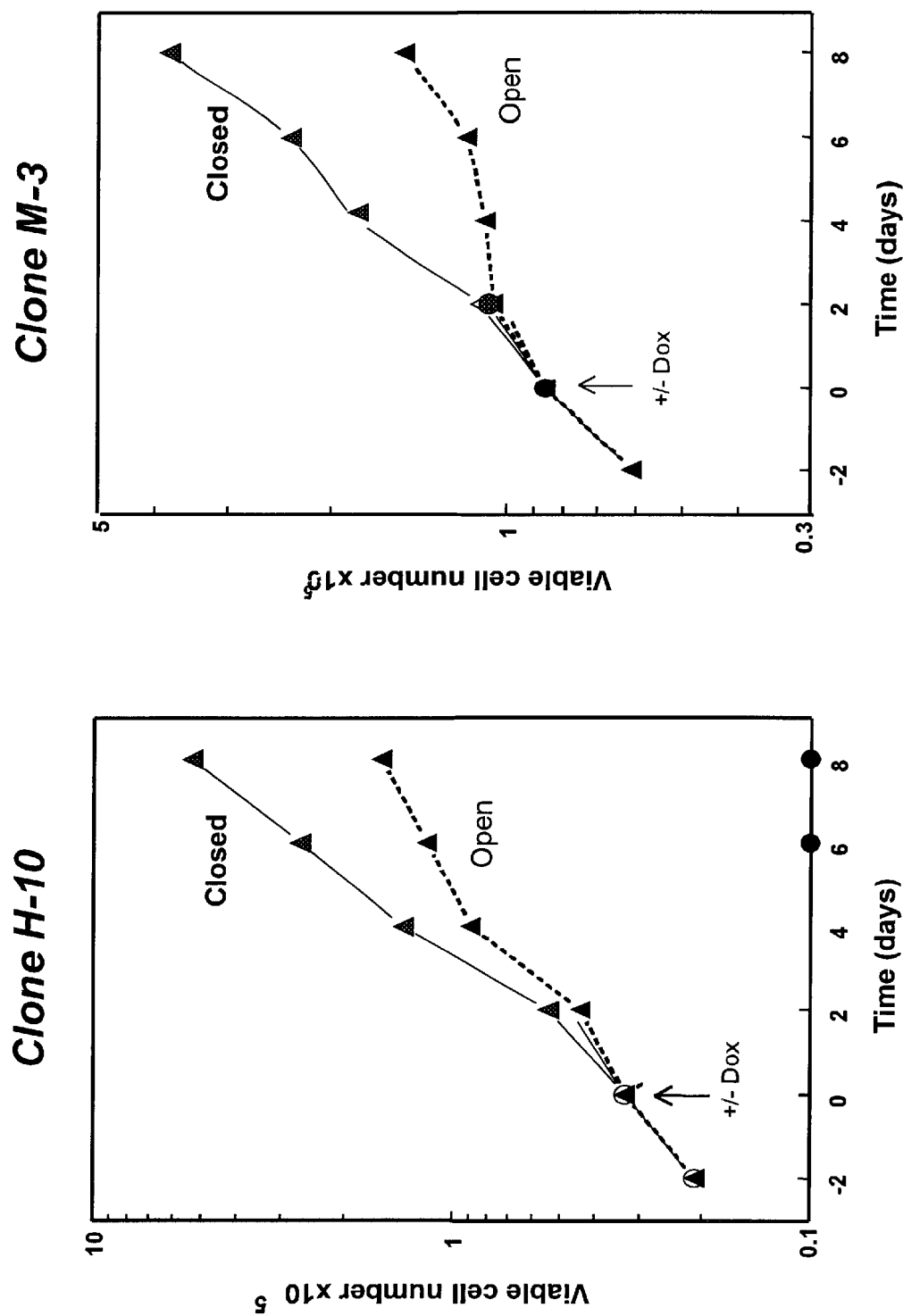
FIG. 7 illustrates the effect of conditional overexpression of SSAT (open) on the growth of clone H-10 cells (transfected with the human SSAT cDNA) and clone M-3 cells (transfected with the murine SSAT genomic sequences).

This embodiment illustrates the effects of SSAT on cell growth.
Effects of SSAT over-expression on Cell Growth FIG. 7 compares the effects of Dox deregulated SSAT activity on the growth of MCF-7 cells transfected with the human SSAT cDNA (clone H-10) or the murine SSAT gene (clone M-3). As with the metabolic studies described above, cultures grown in the presence or absence of Dox for 48 hr were designated as 0 h and curves plotted accordingly. Both the H-10 and M-3 clones became growth inhibited when SSAT was overexpressed. The M-3 cells were more affected and became fully growth inhibited by 4 days minus Dox as opposed to the H-10 cells which showed slowing of cell growth beginning at day 4. Growth effects appeared to be cytostatic as indicated by a sustained lack of growth without an apparent loss in cell number as would be expected with a cytotoxic response.

In the present method, removal of Dox for 48 h resulted in a 5- to 10-fold increase in SSAT activity followed by a distinct inhibition of cell growth. The validity of the finding was reinforced by the fact that it was observed in cells transfected with murine SSAT genomic sequences as well as in cells transfected with the human SSAT cDNA. It is noteworthy that unlike with transgenic fibroblasts (Alhonen et al., 1998, supra) and transfected CHO cells (McCloskey et al., 1998, supra), ODC activity remained unchanged or decreased slightly. Thus, it would appear that when confronted with rapid onset SSAT overexpression, cells are not able to rapidly compensate by increasing polyamine biosynthesis and as a result, they become growth inhibited.

EXAMPLE 5

Figure 8:
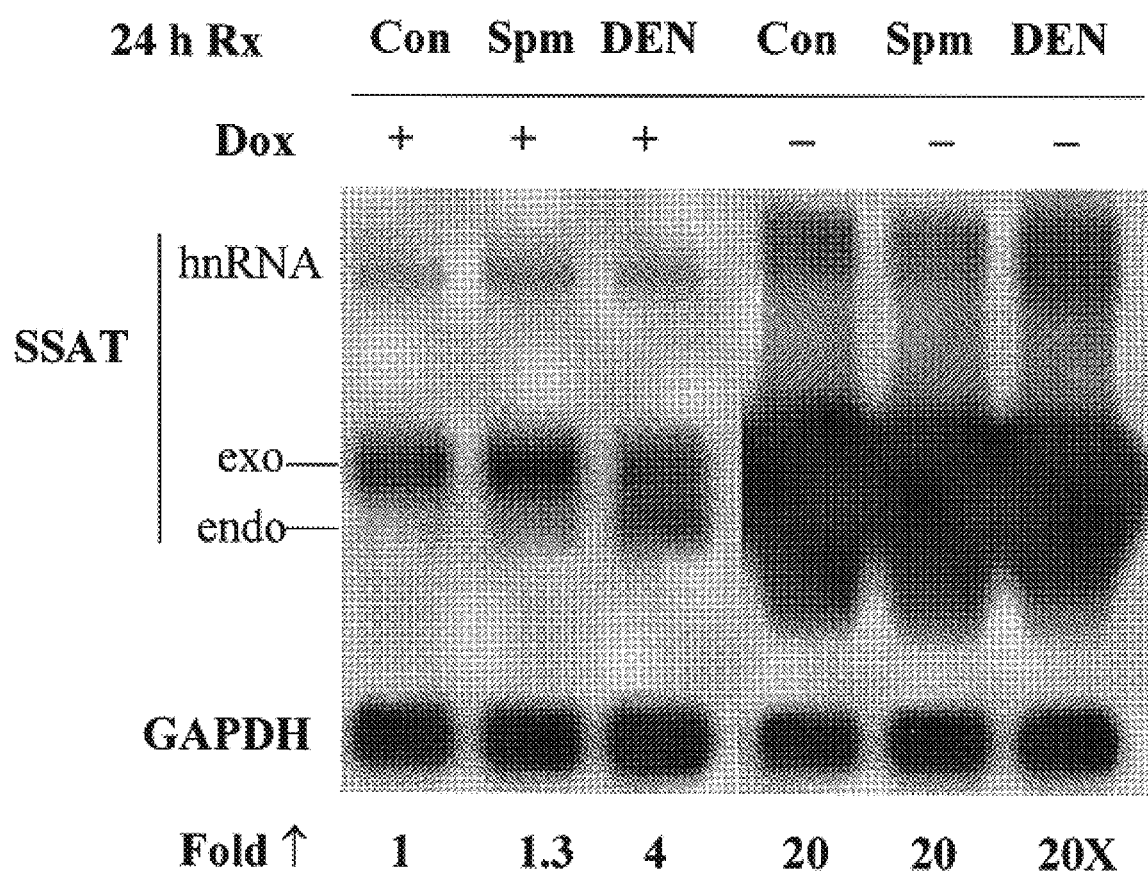
FIG. 8 is a photographic representation of a Northern blot analysis of SSAT mRNA in clone H10 and clone cells showing much greater induction of mRNA in the absence of Dox (open system).

This embodiment demonstrates that DENSPM translationally and post-translationally enhances the expression of SSAT.
DENSPM and Spm Induction of SSAT mRNA and Activity and Polyamine Pools FIG. 8 shows the SSAT mRNA levels in H-10 grown ±Dox for 48 h and then treated with 10 $\mu$M DENSPM or 10 $\mu$M Spm for an additional 24 h. In clone H-10, steady-state levels of SSAT message were ~20-fold higher in −Dox cells and this resulted in a ~5- to 10-fold induction of SSAT activity (Table 2). In this table are presented the effects of conditional overexpression on DENSPM induced SSAT mRNA and activity and on polyamine pool depletion. When exposed to 10 $\mu$M DENSPM for 24 h, MRNA levels increased by 4-fold in induced cells and remained at ~20-fold in uninduced cells. Presumably, some rate-limiting step prevented DENSPM from increasing MRNA beyond the already high levels in these cells. The 4-fold and 20-fold difference in mRNA levels seen in +Dox and −Dox cells resulted in a >80-fold and >1500-fold increase, respectively, in SSAT activity (Table 2). As is known from other systems, DENSPM also suppressed ODC activity in both cells irrespective of SSAT induction and caused a near total depletion of all three polyamines by 48 h.

EXAMPLE 6

This embodiment demonstrates that SSAT overexpression enhances the growth inhibitory effects of DENSPM.

Figure 9:
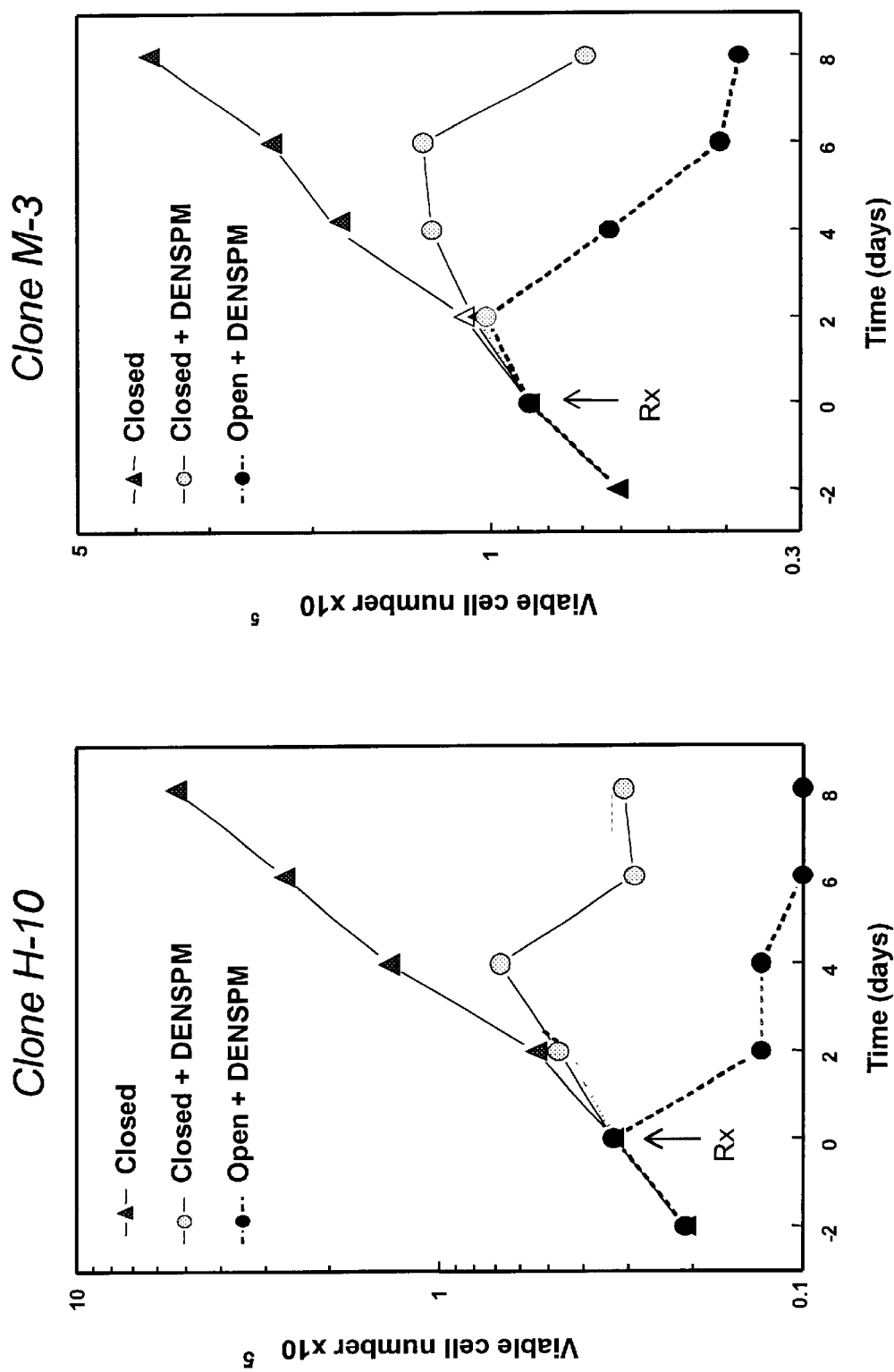
FIG. 9 illustrates the effects of conditional expression of SSAT on the antiproliferative effects of DENSPM in clone H10 and clone M-3 cells.

Relative growth inhibition by DENSPM. The relative antiproliferative effect exerted by DENSPM in H-10 and M-3 cells grown ±Dox was studied over an extended (8 d) time period. As shown in the FIG. 9, H-10-Dox cells were strikingly more sensitive to the antiproliferative action of the DENSPM than +Dox cells. Less than 15% growth inhibition was achieved by 48 h in +Dox H-10 cells compared to >80% in −Dox cells (FIG. 9). A similar difference in response to DENSPM was observed in M-3 cells where growth was inhibited by 25% in uninduced cells and by 78% in induced cells. As a generality, DENSPM-mediated growth inhibition tended to be more cytotoxic during SSAT induction as indicated by the rapid loss in cell number (FIG. 9).

Figure 10:
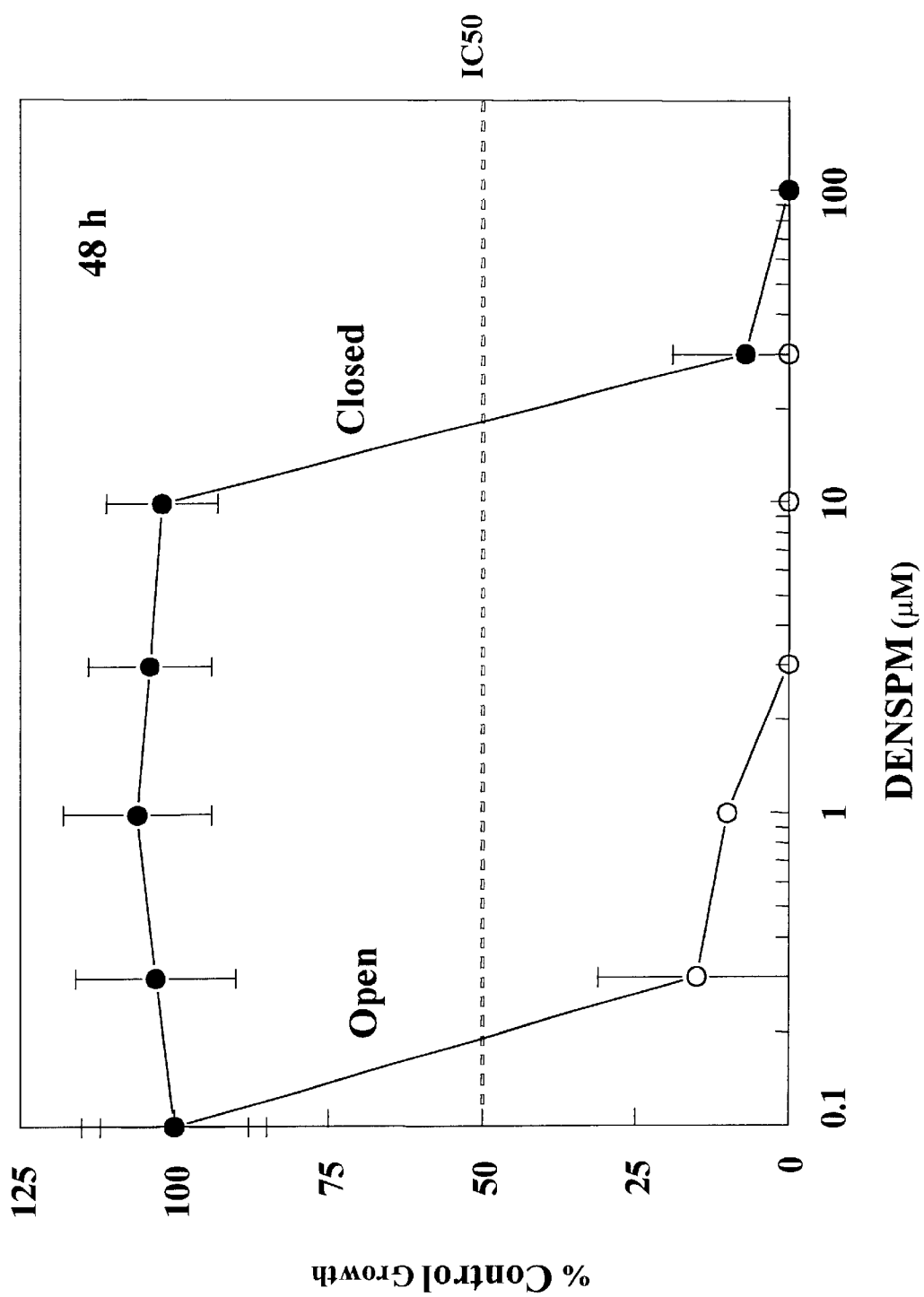
FIG. 10 is a representation of DENSPM dose-response analysis of MCF7/hSc cells +/−Dox (closed vs open).

The increased sensitivity of SSAT induced H-10 cells to DENSPM was quantitated by dose-response analysis. Cells were grown for 48 h ±Dox and then exposed to increasing concentrations of DENSPM for 48 h (FIG. 10). In the $IC_{50}$ comparisons, −Dox cells were about approximately 100-fold more sensitive to DENSPM than +Dox cells (i.e. comparing $IC_{50}$ values of 0.2 and 20 $\mu$M, respectively). The time course data in FIG. 11 indicates that induced cell curves declined more rapidly and to a much lower level than those of the uninduced cells treated with DENSPM.

The overall implications of these studies are that the onset of toxicity occurs earlier and at lower drug concentrations in cells, which overexpress SSAT.

The data presented herein revealed that pure induction of SSAT activity is sufficient to lower polyamine pools and inhibit cell growth. This is in contrast to a previous study using fibroblasts from nontransgenic and transgenic animals that systemically over-expressed SSAT by about 20-fold (Pietila et al., 1997, supra). Although the fibroblasts were differentially sensitive to the growth inhibitory effects of DENSPM, they exhibited nearly identical growth rates (Alhonen et al., 1998, supra) Similarly, comparable growth rates were also seen in parental and SSAT transfected CHO cells (McCloskey et al., 1999, supra). While not intending to be bound by any theory, it is believed that this apparent disjunction with cell growth is related to compensatory metabolic adjustments during embryogenesis and selection, respectively. For example, it is noted that the basal activity of the biosynthetic enzyme ornithine decarboxylase was increased 21-fold in transgenic livers (Pietilä et al., 1997, supra), ~2.6-fold in transgenic fibroblasts (Alhonen et al., 1998, supra) and 3.7-fold in SSAT transfected CHO cells (McCloskey et al., 1998, supra; see FIG. 2). The net effect of such a metabolic adjustment could be to enhance polyamine biosynthesis in response to the increase in polyamine catabolism and excretion brought about by overexpression of SSAT. Both induction of SSAT and growth sensitivity to DENSPM were enhanced in cells in which SSAT expression was up-regulated before and during exposure to the analog and this obviously correlated with SSAT activity. In cells transfected with human SSAT cDNA, DENSPM induced SSAT activity by 1700-fold under −Dox conditions (open) as compared to ~90-fold under +Dox conditions (closed). The dose-response curves described here (FIG. 10) give a quantitative indication of the extent to which DENSPM SSAT induction and growth inhibition are related. As shown in Table 3, a <3-fold difference in basal SSAT mRNA (8 vs 20) translates into a ~20-fold difference in SSAT activity with DENSPM treatment and a 100-fold increase in growth sensitivity to the analog. More specifically, the $IC_{50}$ of DENSPM was lowered from 20 $\mu$M to 0.2 $\mu$M.

It is noteworthy that DENSPM can greatly amplify the SSAT gene response. Expression of SSAT is reported to be transcriptionally and post-transcriptionally regulated (Alhonen et al. 1998, J. Biol. Chem. 273:1964–1969; Fogel-Petrovic et al., 1993, J. Biol. Chem. 268:19118–19125; Fogel-Petrovic et al., 1996, FEBS Lett. 391:89–94; Fogel-Petrovic et al., 1996, Biochemistry 35:14436–14444; Fogel-Petrovic et al.,1997, Molec. Pharm. 52:69–74). Thus, the large levels of SSAT MRNA seen in variously transduced systems (Alhonen et al. 1998, supra) are typically not accompanied by similarly high levels of protein or enzyme activity. As an example, the H-10 clone of MCF-7 cells induced with Dox, display a 20-fold increase in SSAT mRNA but only a 5 to 6-fold increase in enzyme activity. Thus, it appears that SSAT gene expression is translationally repressed by the cell, perhaps for the purpose of avoiding untoward metabolic consequences. However, addition of DENSPM to these cells remarkably changes the level of expressed enzyme protein/activity. In addition to relieving apparent translational repression, the analog markedly stabilizes the protein (half life increases from ~0.5 hr to >6 h) (Libby et al., 1989, Cancer Res., 49:6226–6230). Thus, DENSPM facilitates translation, and more importantly amplifies expression by stabilizing the enzyme protein. The functionality of this stabilized protein is clearly retained as indicated by polyamine depletion of the massive accumulation of acetylated polyamines (Table 1) and this probably accounts for the depletion of the natural polyamine pools (Table 1 and FIG. 7) leading to inhibition of cell growth. A quantitative analysis of these various effects (Table 3) indicated that a 20-fold difference in mRNA results in only a 5–6-fold difference in SSAT activity in the absence of DENSPM and a ~1700-fold increase in SSAT activity in the presence of analog (FIG. 13). Importantly, this enzyme difference translates into a ~100-fold increase in growth sensitivity to the analog.

Analogs would be expected to be equally effective at translationally and post-translationally amplifying SSAT mRNA whether it derives from an exogenously introduced SSAT cDNA or from an endogenous SSAT gene following introduction of exogenous SSAT gene-related transcription factors (Wang et al. supra) or by drugs or therapeutic manipulations which enhance SSAT mRNA (Amundson et al. supra).

The foregoing description of the specific embodiments is for the purpose of illustration and is not to be construed as restrictive. From the teachings of the present invention, those skilled in the art will recognize that the method of the present invention may be modified without departing from the spirit of the invention.

TABLE 1

Effects of conditional SSAT Overexpression on Polyamine Metabolism in H-10 Cells

| Treatment | Rx Time | ODC Activity | SSAT Activity | Polyamine Pools (pmol/10⁶ cells) | | | | |
|---|---|---|---|---|---|---|---|---|
| | | | | Put | AcSpd | Spd | AcSpm | Spm |
| Parental | 48 h | 2.2 | 40 | 250 | 15 | 3,100 | <5 | 2,140 |
| Open | 0 h | 2.1 | 25 | 290 | 20 | 3,265 | <5 | 1,990 |
| | 48 h | 3.1 | 233 | 195 | 680 | 1,025 | 105 | 2,050 |
| | 96 | 2.5 | 210 | 140 | 1,545 | 460 | 140 | 1,880 |

TABLE 2

Effects of conditional SSAT Overexpression on DENSPM Effects

| Treatment (48 h) | SSAT mRNA | SSAT Activity | Polyamine Pools (pmol/10⁶ cells) | | | | |
|---|---|---|---|---|---|---|---|
| | | | Put | AcSpd | Spd | AcSpm | Spm |
| Closed | 1 | 1 | 280 | <5 | 2,365 | <5 | 2,170 |
| +DENSPM | 8 X | 89 X | 50 | 20 | 110 | 50 | 750 |
| Open | 20 X | 5–6 X | 140 | 140 | 460 | 140 | 1,880 |
| +DENSPM | 20 X | 1,700 X | <5 | <5 | <5 | 20 | 65 |

TABLE 3

Effect of SSAT Expression on DENSPM Anti-Proliferative Responses

| Treatment | SSAT Effects | | Growth Effects | |
|---|---|---|---|---|
| | mRNA (fold) | Activity (fold) | Onset of cytotoxicity | IC50 Dose ($\mu$M) |
| Dox, 200 ng/ml; DENSPM, 10 $\mu$M, 48 h) Closed | | | | |
| No Rx | 1 | 1 | — | — |
| +DENSPM | 8X | 89X | 4 days | 200 $\mu$M |
| Open | | | | |
| No Rx | 20X | 5–6X | — | — |
| +DENSPM | 20X | 1700X | immediate | 0.2 $\mu$M |

What is claimed is:

1. A method of inhbiting the growth of cells in vitro comprising inducing spermidine spermine $N^1$ acetyltransferase (SSAT) mRNA by transfecting cells with SSAT cDNA under the control of a regulatable promoter and regulating the promoter to induce production of SSAT mRNA, wherein cell growth is reduced over cells in which SSAT mRNA is not induced.

2. The method of claim 1 further comprising the step of exposing the cells to a polyamine analog.

3. The method of claim 2, wherein the polyamine analog is $N^1$, $N^{11}$-diethylnorspermine (DENSPM).

* * * * *